(12) United States Patent
Forsell (10) Patent No.: US 8,900,514 B2
(45) Date of Patent: Dec. 2, 2014

(54) DEVICE FOR DETERMINING THE ERYTHROCYTE SEDIMENTATION RATE IN A BLOOD SAMPLE

(76) Inventor: Tommy Forsell, Uppsala (SE)

( * ) Notice: Subject to any disclaimer, the term of this patent is extended or adjusted under 35 U.S.C. 154(b) by 997 days.

(21) Appl. No.: 12/676,308

(22) PCT Filed: Sep. 1, 2008

(86) PCT No.: PCT/SE2008/050980
§ 371 (c)(1),
(2), (4) Date: Mar. 3, 2010

(87) PCT Pub. No.: WO2009/031969
PCT Pub. Date: Mar. 12, 2009

(65) Prior Publication Data
US 2010/0196945 A1 Aug. 5, 2010

(30) Foreign Application Priority Data
Sep. 4, 2007 (SE) ...................................... 0702039

(51) Int. Cl.
*G01N 33/00* (2006.01)
*C12Q 1/68* (2006.01)
(Continued)

(52) U.S. Cl.
CPC .............. *G01N 21/59* (2013.01); *G01N 21/251* (2013.01); *G01N 21/11* (2013.01); *G01N 15/05*
(Continued)

(58) Field of Classification Search
CPC ... G01N 11/04; G01N 21/0303; G01N 21/31; G01N 33/4905; G01N 15/05; G01N 2021/054; G01N 2021/3144; G01N 21/11; G01N 21/251; G01N 21/59

USPC .......... 422/50, 400–405, 417, 419, 425, 430, 422/62, 68.1, 73, 82.05, 82.09, 91, 92, 422/500–504, 509, 547, 549, 551, 554, 422/558–566
See application file for complete search history.

(56) References Cited

U.S. PATENT DOCUMENTS

| 3,847,482 A | 11/1974 | Sokol et al. |
| 5,827,746 A | 10/1998 | Duic |
| 6,336,358 B1 | 1/2002 | Kishimori et al. |

FOREIGN PATENT DOCUMENTS

| DE | 2631291 A1 | 1/1978 |
| GB | 2 093 985 A | 9/1982 |

(Continued)

OTHER PUBLICATIONS

Kalchenko et al. (In vivo dynamic light scattering imaging of blood coagulation, Journal of Biomedical Optics 12(5), 052002 (Sep./Oct. 2007)).*

(Continued)

*Primary Examiner* — Dean Kwak
(74) *Attorney, Agent, or Firm* — Birch, Stewart, Kolasch & Birch, LLP (57) ABSTRACT

The invention discloses a blood analyzing device (100) comprising a holder (110) arranged for carrying a container (10) having a cuvette (20) containing a blood sample (30). The container (10) is positioned in the holder (110) so that a longitudinal axis (60) of the cuvette (20) is angled relative a horizontal axis (70). A light source (120) provides light (40) into the sample (30) and a detector (130) detects the output light (50) from a sub-portion of the blood sample (30). Kinetic information indicative of the change in hemoglobin concentration in a measuring volume (32, 34) is determined by a Hb processor (145) from the detected output light (50). An ESR processor (140) determines the erythrocyte sedimentation rate of the sample (30) based on the kinetic information.

11 Claims, 10 Drawing Sheets

(51) Int. Cl.
*G01N 21/75* (2006.01)
*B01L 3/00* (2006.01)
*B01L 3/02* (2006.01)
*G01N 21/25* (2006.01)
*G01N 21/11* (2006.01)
*G01N 21/59* (2006.01)
*G01N 15/05* (2006.01)
*G01N 21/05* (2006.01)
*G01N 21/31* (2006.01)

(52) U.S. Cl.
CPC .. (2013.01); *G01N 2021/054* (2013.01); *G01N 2021/3144* (2013.01)
USPC .............. 422/73; 422/50; 422/400; 422/401; 422/402; 422/403; 422/404; 422/405; 422/417; 422/419; 422/82.05; 422/82.09; 422/91; 422/92; 422/500; 422/501; 422/502; 422/503; 422/504; 422/509; 422/547; 422/549; 422/551; 422/554; 422/560; 422/561; 422/565; 422/566

(56) References Cited

FOREIGN PATENT DOCUMENTS

| JP | 59-147265 A | 8/1984 |
| JP | 2001-46360 A | 2/2001 |
| JP | 2004-125650 A | 4/2004 |
| WO | WO 98/02726 A1 | 1/1988 |
| WO | WO 91/05996 A1 | 5/1991 |
| WO | WO 2006/104451 A1 | 10/2006 |

OTHER PUBLICATIONS

Savateeva, et al. "Optical properties of blood at various levels of oxygenation studied by time resolved detection of laser-induced pressure profiles", SPIE Proceedings, vol. 4618; 2002; pp. 63-75; XP-002342829.

* cited by examiner

DEVICE FOR DETERMINING THE ERYTHROCYTE SEDIMENTATION RATE IN A BLOOD SAMPLE

TECHNICAL FIELD

The present invention generally relates to blood analysis, and in particular to a blood analyzing device capable of determining an erythrocyte sedimentation rate in a blood sample and uses thereof.

BACKGROUND

Blood is commonly described as a complex red fluid consisting of plasma with a suspension of blood cells, mainly red blood cells. In an adult the blood volume is approximately 5 liters, of which 40-50% is red blood cells. The ratio between red cells and plasma is called hematocrit. Plasma consists mainly of water with proteins, sugar, vitamins, hormones, etc. A red blood cell, or erythrocyte, consists of a thin membrane as a kind of balloon in which there is water and a high concentration of the protein hemoglobin (Hb) in various forms. Hemoglobin is complex molecule containing heme groups with iron atoms that can bind to and release oxygen and carbon dioxide in the circulation. Normally there is approximately 13-15 g hemoglobin per 100 ml blood in an adult, corresponding to 4-5 million red blood cells. Even a very small sample of blood taken from one person is a representative amount of blood cells for making measurements to determine certain properties and conditions of the blood. The hemoglobin value is a representation of the oxygen transportation capacity of the blood to other tissue and a parameter for patient diagnosis. Hemoglobin value is furthermore a primary safety and quality parameter in blood banking where blood is stored for transfusion purpose and collected as raw material for blood based industrial purposes.

Hemoglobin measurement is one of the most common diagnostic tests in the world today. Recently, development has taking place in the field of hemoglobin measurement, in that whole blood can be used as measurement material, thereby relaxing the need for hemolysation. An example of such an improved hemoglobin measuring device is disclosed in the International patent application number WO 2006/104451.

In addition to determining hemoglobin in a blood sample, other blood tests are routinely employed in primary care diagnosis. An example of such additional test is erythrocyte sedimentation rate (ESR). This ESR rate is a non-specific measure of inflammation, which is commonly used as a medical screening test. Today, the test is performed by placing anti-coagulated blood in an upright Westergren tube and the rate at which the red blood cells fall is measured in mm/h. When an inflammatory process is present, the high proportion of protein, e.g. fibrinogen and immunoglobulins, in the blood causes the red blood cells to stick to each other. The red blood cells form stacks called "rouleaux" which settle faster than individual red blood cells, thereby resulting in a higher ESR rate in the case of inflammation.

U.S. Pat. No. 6,336,358 discloses a device for measuring the sedimentation rate or erythrocytes in a sample. A test container is filled with the blood sample and is inclined and held at the specific inclination angle during the test. Light is projected into the container and the light passing through the container is electrically detected by a line sensor. The detector reading is used for determining the liquid level of the supernatant in the sample and the position of the boundary between the supernatant and the sediments. The ESR can then be calculated based on the supernatant level and the position of the boundary.

SUMMARY

The prior art ESR measurement is a cumbersome and time-consuming test. The improvement present in U.S. Pat. No. 6,336,358 reduces the time required for the ESR test to about one quarter. However, the reduced test time is still about 15-20 minutes, which is quite long. Furthermore, medical testing and diagnosis would significantly benefit from a possibility of measuring hemoglobin and ESR in the same blood sample container.

The present invention overcomes these and other drawbacks of the prior art arrangements.

It is a general object of the present invention to provide a spectrophotometry based ESR determination.

It is another general object of the present invention to provide a blood analyzing device capable of determining erythrocyte sedimentation rate even in a small blood sample volume.

It is a further general object of the present invention to provide an ESR determination without requiring an extensive test time period and without the need for a manual reading following expire of the test time period.

It is particular object of the invention to provide a blood analyzing device capable of determining both a hemoglobin measure and erythrocyte sedimentation rate in a single blood sample container.

These and other objects are met by the invention as defined by the accompanying patent claims.

Briefly, the present invention involves a blood analyzing device comprising a holder arranged for carrying a container having a cuvette comprising a blood sample. The holder carries the container in a measuring position, in which a longitudinal axis of the cuvette is angled with a non-zero angle relative a horizontal axis. At this position a light source provides input light into the blood sample. The input light is selected to contain at least one wavelength at which at least one hemoglobin species presents high absorbance. A light detector is arranged for detecting resulting output light originating from a measuring sample volume constituting a sub-portion of the total blood volume in the cuvette. An Hb processor is connected to the light detector and determines kinetic Hb information based on the output light detected by the light detector. This kinetic information represents the change in red blood cell concentration or Hb over time in the measuring volume. An ESR processor uses this determined kinetic information for providing the erythrocyte sedimentation rate (ESR) in the blood sample.

In a preferred embodiment, the blood analyzing device also determines at least one hemoglobin (Hb) parameter in the same blood sample in the cuvette, in addition to the ESR value. This Hb parameter can be total Hb concentration in the blood and/or at least one fractional Hb concentration. In such a case, the blood analyzing device first performs spectroscopic measurements for determining the Hb parameter before the red blood cells have sedimented. Once the Hb measurement has been completed, the device can perform the spectroscopic ESR measurements, possibly using at least a portion of the Hb measurement results. The Hb parameter can also be used in the ESR determination for the purpose of providing an Hb-normalized ESR measure. The spectroscopic Hb-measurements do not necessarily have to be conducted with the cuvette being angled. In such a case, the container is placed in the holder in an initial Hb-measuring position. Once the Hb measurements have been completed, the container can be moved so that the cuvette is placed in the correct sloping measurement position.

The present invention also relates to a blood analyzing method for the purpose of determining an ESR value in a blood sample and preferably for determining both an ESR value and an Hb parameter in the same blood sample.

SHORT DESCRIPTION OF THE DRAWINGS

The invention together with further objects and advantages thereof, may best be understood by making reference to the following description taken together with the accompanying drawings, in which.

DETAILED DESCRIPTION

Throughout the drawings, the same reference characters will be used for corresponding or similar elements.

The present invention generally relates to a novel device and method for determining the erythrocyte sedimentation rate (ESR) of a blood sample based on a spectrophotometric technique. This technique allows usage of much smaller blood sample volumes as compared to the prior art ESR measurements. In addition, the time from starting the measurement until the final ESR measure is available is radically reduced by the present invention. A further advantage of the invention is that it allows determination of Hb-compensated or -normalized ESR readings.

The present invention is based on the phenomenon that when a blood sample is introduced into a cuvette of the present invention (or indeed in any blood sample container in vitro), the red blood cells in the blood tend to stick to each other forming cell stacks or rouleaux. These cell stacks will sediment towards the bottom of the cuvette at a much higher rate than individual cells. This will over time cause a depletion of red blood cells in the top of the cuvette and an accumulation of blood cells in the bottom of the cuvette. There will then be a gradient in local red cell concentration when going from the cuvette top (low concentration) towards the cuvette bottom (high concentration).

The red blood cells contain hemoglobin in different forms, including oxy-, deoxy-carboxy-, met- and sulfhemoglobin. In addition, the cells can contain bilirubin, a breakdown product of the normal heme catabolism. All these molecules are pigments and can be detected through spectrophotometry.

Thus, the present invention uses a spectrophotmetric approach of determining the ESR by following or detecting the sedimentation of the red blood cell stacks in the sample. The invention therefore uses spectrophotometric data for monitoring the kinetics in the change of Hb or red blood cell concentration and using this kinetic information in determining the ESR.

Figure 1:
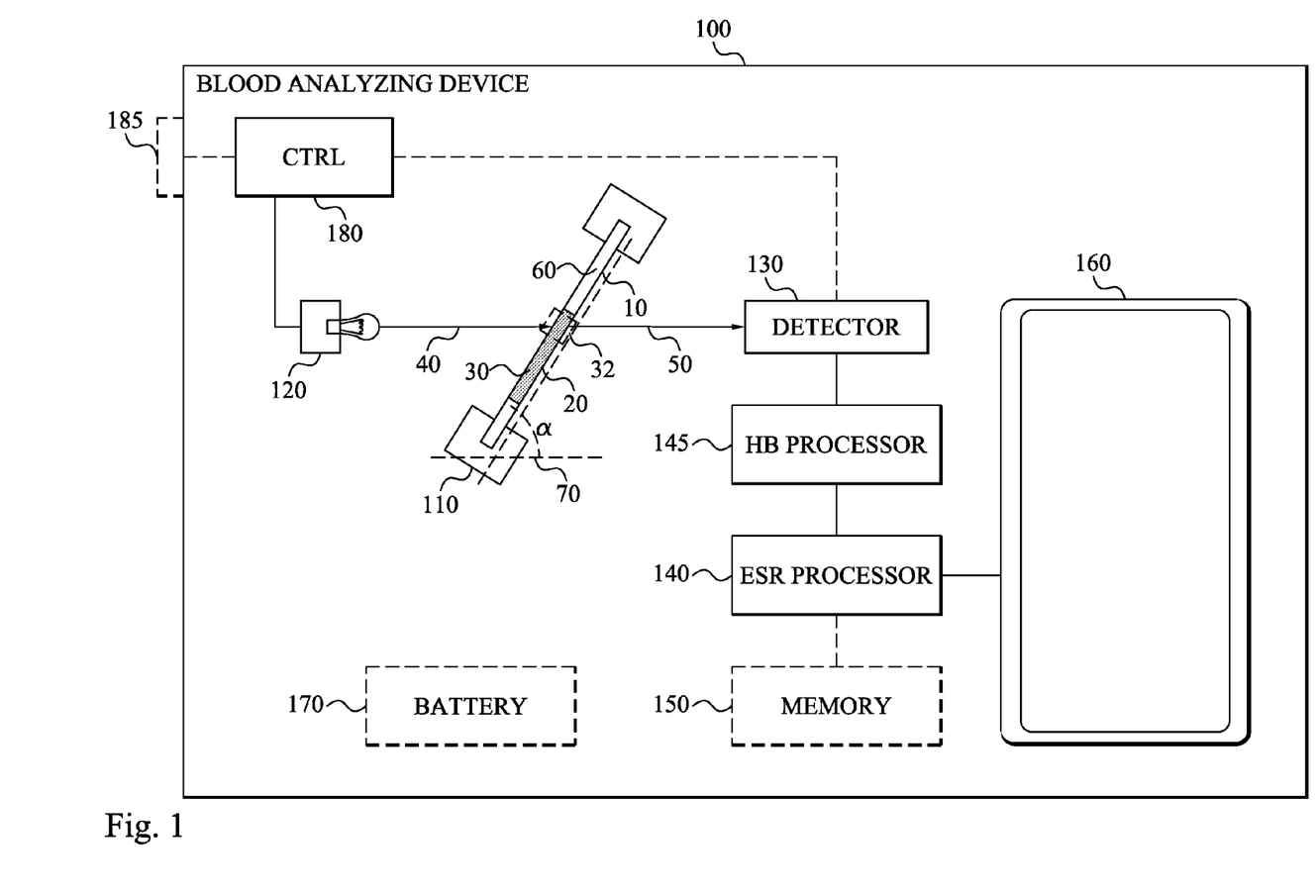
FIG. 1 is a block diagram illustrating a blood analyzing device according to an embodiment of the present invention.

FIG. 1 is a schematic block diagram of a blood analyzing device 100 according to the present invention adapted for determining the ESR of a blood sample.

A sample container 10 having a cuvette 20 containing a blood sample 30 is introduced in a holder 110 of the device 100. The cuvette 20 is generally in the form of a so-called microcuvette in that the total size of the container 10 and the blood sample is very small. The cuvette 20 has a longitudinal extension in a first dimension and a comparatively shorter extension in a second dimension. The extension in the third dimension could be equal to or longer than the extension in the first dimension, equal to or shorter than the extension in the second dimension or between the extensions in the first and second dimension.

The holder 110 of the device 100 is arranged for carrying the container 10 in a measuring position, in which a longitudinal axis 60 of the cuvette 20 is angled relative a horizontal axis 70. Thus, the container 10 and its cuvette 20 is arranged in this measuring position so that there is a non-zero angle α between longitudinal axis 60 of the cuvette 20 and the horizontal axis 70. The longitudinal axis 60 is the axis of the longitudinal side in the first dimension of the cuvette 20.

If the cuvette 20 would have been placed in the horizontal plane, i.e. the longitudinal axis 60 is parallel with the horizontal axis 70, it could have be possible to spectrophotometrically detect the red blood cell sedimentation in the sample 30 by providing the input light 40 vertically. However, the result of any such spectrophotometric measurement would give inferior and insecure ESR values.

If the light 40 instead would be provided horizontally into blood sample 30 i.e. using a thick cuvette 20, the light will travel a long distance in the blood sample 30. The many particles and cells present in the sample 30 will cause extensive light scattering and multi-paths of the light in the sample 30. This increases the processing complexity, when determining the ESR based on absorbance measurements of the detected output light.

Therefore, the angle α between the two axes 60, 70 of the present invention is larger than 0° and preferably smaller than 90°. Preferably, the angle α is in an interval of from about 25° to about 80°. More preferably, the angle α is preferably from about 45° to about 60°.

By placing the cuvette 20 in a non-zero angle α relative the horizontal plane or axis 70 but in an angle α less than 90°, the gradient in red blood cell sedimentation appears much faster than by placing the cuvette 20 vertically (longitudinal axis 60 perpendicular to the horizontal axis 70). This will greatly reduce the measuring time for determining the ESR in the blood sample 30.

The blood analyzing device 100 also comprises a light source 130 arranged for directing input light 40 into the blood sample 30. This directed light 40 preferably incident in a defined measuring volume 32 of the blood sample 30. This measuring volume 32 constitutes a sub-portion of the total blood volume in the cuvette 20. However, it could alternatively be possibly to guide the light 40 from the light source 120 towards a major or even total area of the blood 30 in the cuvette 10 facing the incoming light 40.

A light detector 130 is arranged for detecting output light 50 from the measuring volume 32 of the blood sample 30 in the cuvette 20. Thus, even though the input light 40 might fall onto the whole or major blood sample surface, the detector 130 is arranged for detecting the output light 50 originating from a sub-portion of the blood sample 30, i.e. the measuring volume 32.

Figure 12:
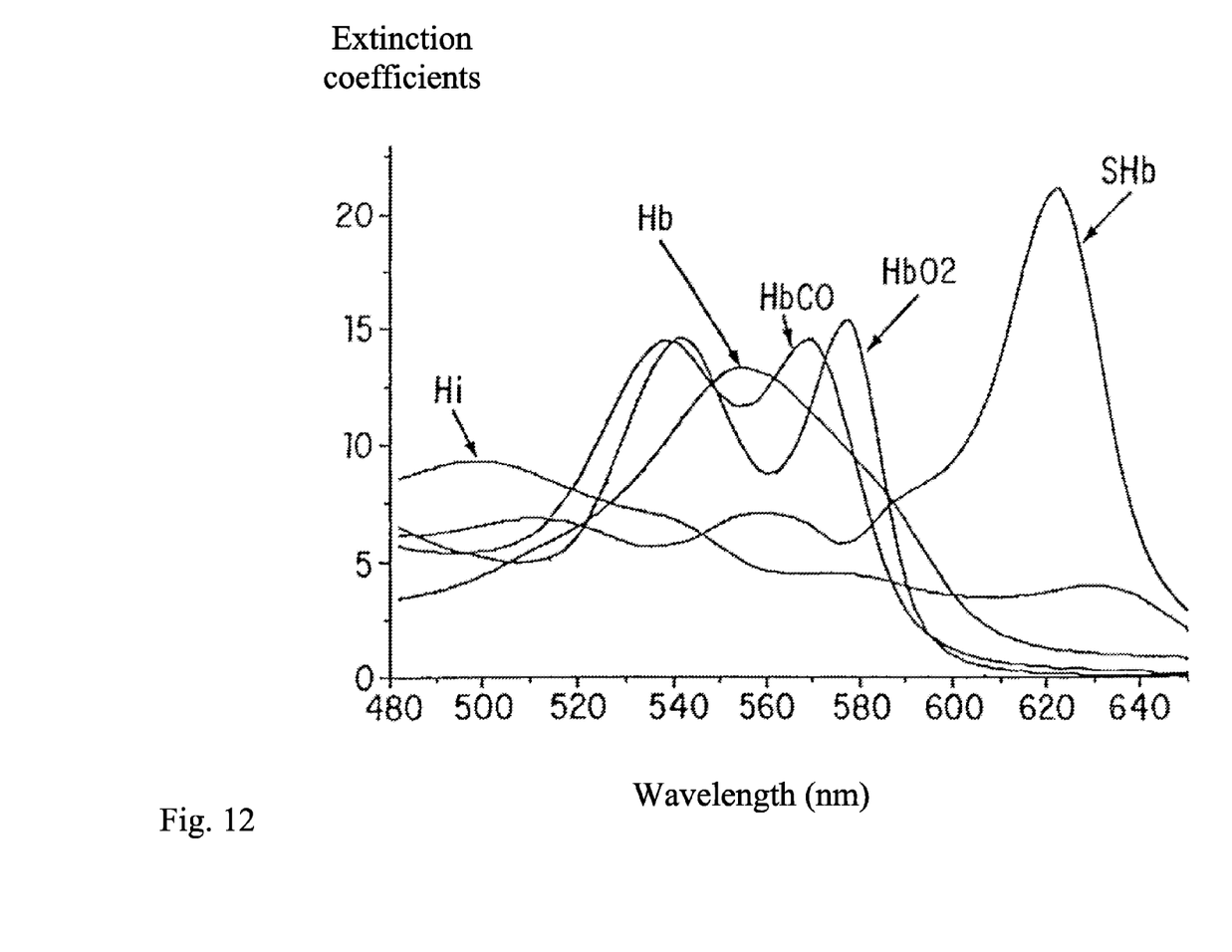
FIG. 12 is a diagram of absorbance spectra for five primary hemoglobin species.

The light source 120 could be a monochromatic light source providing light at a wavelength causing an absorbance of red blood cell stacks (rouleaux) in the blood sample 30. Such a wavelength could be a wavelength for which hemoglobin (one of the hemoglobin species or bilirubin) in the red blood cells has maximum absorbance or at least close to maximum absorbance. The detector 130 is then a general photometer that can detect the absorbance, transmittance or reflectance at that particular wavelength. Hemoglobin can be present in one of the multiple species. In the art, the main such Hb species are oxyhemoglobin ($HbO_2$), carboxyhemoglobin (HbCO), methemoglobin or hemoglobin (Hi), reduced hemoglobin (Hb) and sulfhemoglobin (SHb). FIG. 12 is a diagram illustrating the absorbance spectra for these five Hb species. As is seen in the diagram, SHb has maximum absorbance close to 625 nm, $HbO_2$ close to 540 nm and 577 nm, HbCO close to 538 nm and 570 nm, Hb close to 555 nm and Hi close to 500 nm. The light provided by the light source 120 is therefore preferably selected to be close to any of these maximum absorbance wavelengths.

However, it might also be advantageous to have a reference wavelength or using multiple wavelengths in order to provide a more accurate representation of the ESR measure. The present invention can be regarded as detecting the turbidity in the blood sample 30, where this turbidity is caused by the (red) blood cells present therein.

For example, the light source 120 could be a broad band light source, providing white light, preferably with a continuous wavelength spectrum within the whole or part of the wavelength range 350 to 900 nm. The detector 130 could then be in the form of a spectrophotometer registering the light intensity of the output light as a function of wavelength. A possible implementation of such a detector 130 is a monolithic multi-wavelengths diode array. The relevant wavelength window then preferably covers at least one of the above-mentioned hemoglobin maximum absorbance wavelengths.

Alternatively, the light source 120 could be a variable wavelength monochromatic light source being able to provide in a sequence of multiple separate wavelengths, preferably in the range of 350 to 900 nm. The detector 130 could then be a standard photometer registering absorbance, transmittance or reflectance of the output light 50.

The present invention can be used in connection with different known light source embodiments 120 including, but not limited to, LED, laser, flash types.

As will described in more detail below, the detector 130 can be arranged for performing detection/measurements on output light 50 having passed through the blood sample 30 in the cuvette 20. Thus, the detector 130 could then detect absorbance/transmittance at one or more wavelengths in the output light 50. Alternatively, the detector 130 can be arranged for detecting reflected output light 50 from the measuring volume 32 of the sample 30.

The blood analyzing device 100 also comprises a Hb processor 145 connected to the detector 130 and arranged for processing the output data of the detector 130 provided based on the output light 50 detected by the light detector 130. The Hb processor 145 generates kinetic information representative of a change in concentration of at least one monitored Hb species and thereby a change in red blood cell concentration over time in the measuring volume 32. This kinetic information, thus, reflects the process in which the red blood cells form stacks and starts sediment towards the bottom of the cuvette 20. When the blood cells sediments in the upper layer of the blood sample 30, i.e. in the measuring volume 32, the number of blood cells in this volume 32 diminishes and thereby the Hb value and the red blood cell concentration in the volume 32 also diminishes over time.

The Hb processor 145 therefore determines the kinetic information from the detector readings at multiple, i.e. at least two, separate reading points of time. The change in concentration could then simply be expressed as the difference in absorbance (proportional to Hb concentration) divided by the time elapsed between the two measuring points of time. However, more elaborated techniques for determining the kinetic data using more than two detection readings can of course be used and are generally preferred.

The Hb processor 145 is connected to an ESR processor 140 arranged for processing the kinetic information from the Hb processor 145. Thus, the processor 140 is able to determine the ESR in blood sample 30 based on the kinetic information and therefore based on the change in red blood cell concentration or Hb over time in the measuring volume as determined based on the detected output light 50.

The ESR processor 140 preferably has access to an algorithm or conversion/mapping function that is employed for calculating the ESR value based on the provided input data, i.e. measured kinetic absorbance/transmittance/reflectance data. Alternatively, the processor 140 can have access to a standardized table, standard curve or database of standard ESR values and corresponding kinetic values. Thus, such a table/curve/database can then be used for mapping a determined Hb kinetic value to an ESR value.

In a particular embodiment, as ESR values traditionally differ based on sex (women generally having higher ESR than men), age (older people generally has higher ESR than younger) and race (black population generally has higher ESR than white population), the algorithm of the ESR processor 140 can use further such age, sex and/or race data as input data when performing the ESR calculation. Alternatively, the processor 140 has multiple different standard tables/curves/databases adapted for women and men, different age intervals and/or the race of the patient from which the blood sample has been taken. In such a case, the blood analyzing device 100 preferably comprises a user input, e.g. in the form of a touch sensitive screen 160 or dedicated hard user input, for setting sex, age and/or race of the patient from which the blood has been taken. The ESR processor 140 processes an input signal generated based on the activation of the user input and selects the correct standard table/curve/database based on that input signal or the algorithm uses the input signal in the ESR calculation.

The standard table/curve/database or the different tables/curves/databases can have been generated in a calibration procedure of the blood analyzing device 100. In such a case, ESR values are determined in blood samples, preferably, from multiple different subjects both with the prior art standard ESR method and with the blood analyzing device 100 of the present invention. The detector values obtained from the device 100 can then be used for determining corresponding Hb kinetic values that are correlated to the traditionally measured ESR values to provide a correlation therebetween.

A standard table/curve/database can then be generated and stored in a memory 150 in signal connection with the HSR processor 140. A similar calibration procedure can be employed as a basis for generating the conversion algorithm, if such an algorithm is implemented (in hardware, software or a combination of hardware and software) in the blood analyzing device 100.

In the figure, the Hb processor 145 and the ESR processor 140 have been illustrated as separate entities. In another embodiment of the invention, the respective functionality of these two processors 140, 145 are combined and included in a single processor of the blood analyzing device. Thus, the usage of a Hb processor 145 and an ESR processor 140 should be reflected as having two processing functionalities that may residence in one or two processor entities.

Once the ESR processor 140 has determined the ESR value of the current blood sample, the result can be presented on a display screen 160 of the device 100 for review of a user, e.g. a physician, other medical personnel or indeed the patient himself/herself. In addition, to merely displaying an ESR value, the processor can be arranged for comparing the determined ESR values with normal ESR values. The normal values could be an average ESR representation for the general population. Alternatively, the normal ESR value or normal ESR value range can be selected based on the age, sex and/or race of the person from which the blood sample has been taken. In the case of a large difference between the determined value and the normal range, the processor can display an alarm alert on the display screen 160, for example if the ESR value is larger than normal. The display screen 160 can also display a normal indication if the measured value is within the normal ESR range, display a high indication if the measured value exceeds the normal range and display a low indication if the measured value falls below the normal range.

The ESR processor 140 can also or instead store the determined ESR value in a connected memory 150 for display or retrieval at a later time. If the blood analyzing device 100 comprises or can be connected to a communication unit, possibly a wireless communication unit, the determined ESR value can be sent from the device 100 to a remote location, e.g. a physician's office.

The blood analyzing device 100 typically also comprises a battery 170 or some other power source, providing the power required for operating the other including elements of the device 100. It is anticipated by the present invention that the battery 170 can be replaced by an external power source, connected to the device 100 through a power cord.

The spectroscopic measurement of the blood analyzing device 100 could be started automatically once the sample container 10 has been placed in the holder 110 or once the container 10 is in the measuring position with the longitudinal axis 60 of the cuvette 20 angled relative the horizontal axis 70. In such a case, a control unit 180 can selectively switch on the light source 120 and/or active the detector 130 when a predefined time period has elapsed from the container positioning. In such a case, the ESR measurement is defined to take place once the red blood cells and stacks have been allowed to sediment for a predefined period of time, e.g. one or a few minutes but even sub-minute periods are possible. The blood analyzing device 100 is through the operation of the controller 180 consistent in the measuring time in that for each and every ESR measurement a relevant detector reading is obtained when the predefined time period from the positioning moment has lapsed.

Instead of having an automatic initiation of the spectroscopic measurements, the blood analyzing device 100 can be equipped with an activation input 185, non-limitedly illustrated in the form of a push button 185 in the figure. The user of the device 100 will then active the input 185, which causes the generation of an activation signal that is forwarded to the controller 180. The controller 180 activates the light source 120 and the detector 130 for performing an ESR reading in the blood sample 30. In this setting, the user can have been instructed to activate the measurement after a predefined time period as has lapsed following the introduction of the container 10 in the device 100 (and holder 110).

In a preferred approach, the blood analyzing device 100 is configured for performing multiple separate spectroscopic measurements at multiple different time instances. For example, a separate detection can be performed every $10^{th}$ second, every $20^{th}$ second, every $30^{th}$ second or every minute in a time frame of up to, for instance, 1 minute, 2 minutes, 3 minutes, 4 minutes, 5 minutes, 6 minutes, 7 minutes, 8 minutes, 9 minutes or 10 minutes. In most practical implementations, it could be enough to perform measurements every $10^{th}$, $20^{th}$ or $30^{th}$ second up to 2-5 minutes. This should be compared to the traditional ESR test that may have a test period of up to one hour before reading the ESR value.

The Hb processor 145 can use all of these multiple detector readings or at least a portion therefore in the determination of the kinetic information reflecting the change in Hb over time in the measuring volume. Thus, the blood analyzing device 100 will then according to this particular embodiment generate further valuable diagnostic information that is not obtainable by the ESR determination of the prior art. In other words, both kinetic information reflective of how the sedimentation proceeds over time and ESR data are provided by the analyzing device 100.

A particular embodiment of the device 100 could be switched between two operational modes, one that gives a single ESR value and another one that also provides ESR kinetic data. In the former mode, a few measurements are enough to get the ESR value. However, in the kinetic mode, the device 100 is configured for performing a series of multiple measurements. The user can then select the particular operation mode, typically by activating a user input 185.

In a preferred embodiment of the present invention, the blood analyzing device 100 is able to determine not only the ESR value in the blood sample 30 but can also perform hemoglobin (Hb) measurements in the sample 30.

In such a case, the relevant Hb measure is determined by the Hb processor 145 shortly following placing the container 10 in the correct measurement position in the holder 110. At this early stage of the measurements, the sedimentation of the blood cells has not had time to initiate or has only progressed for a short period of time. As a consequence, one or multiple of the first detector readings by the detector 130 is preferably used by the Hb processor 145 for determining the relevant Hb parameter. Subsequent detector readings are then used, preferably together with the first one(s), in order to provide the kinetic information of the Hb changes.

A preferred approach, the light detector 130 is arranged for detecting, at least once within a measuring time interval following positioning of the container 10 in the holder 110, output light 50 having passed through the blood sample 30. The input light 40 is allowed to pass through the sample 30 in the comparatively shorter extension of the cuvette 20. The input light therefore incidence on an input area defined by the previously mentioned first and third dimension of the cuvette 20.

Thus, for Hb measurement the detector 130 determines the absorbance or transmittance at different wavelengths (or frequencies) in the output light 50. The light source 120 can have the same settings as for ESR measurements, e.g. provide light over a whole wavelength spectrum (white light) or sequentially provide monochromatic light at different wavelengths. In the latter case, the separate wavelengths preferably correspond to the wavelengths of maximum absorbance for the different Hb species.

The Hb processor 140 will then processes the measurement results for the purpose of determining the total Hb concentration (amount) in the blood sample 30 and/or at least one Hb fraction.

The Hb measurements are preferably conducted with a blood sample 30 that is homogenous or close to homogenous. Thus, if the container 10 is directly placed in the measuring position with a non-zero angle α between the longitudinal axis 60 and the horizontal axis 70, the Hb measurements are preferably performed immediately following the placement of the container 10 in the holder 110 or at least shortly after the positioning, such as within about 5 seconds, preferably about 2 seconds. During this short period of time, the cell stacks will only have had time to sediment marginally, implying that the sample 30 is still close to homogenous.

In an alternative approach the holder 110 comprises a movable holder portion allowing the container 10 to be moved between a loading position and the ESR-measuring position. In such a case, the initial Hb measurement can be conducted in the loading position or in a dedicated Hb-measuring position. In order to reduce the risk of cell stack sedimentation before the Hb measurements, the container 10 could positioned in the loading or dedicated Hb-measuring position so that the longitudinal axis 60 is substantially parallel with the horizontal axis 70. Once the detector 130 has performed the light detection required for Hb concentration determination, the container 10 can be moved, such as rotated, into the ESR measuring position, in which the longitudinal axis 60 is angled relative the horizontal axis 70.

The ESR value of a blood sample depends, at least to some extent, on the number of red blood cells or the Hb concentration in the blood. The blood analyzing device 100 of the present invention can obtain such an Hb concentration prior the ESR measurements. This means that the determined Hb parameter, such as total hemoglobin or at least one Hb fraction, can be used by the ESR processor 140 when determining the ESR based on the kinetic information. The relevant Hb parameter has previously been determined by the Hb processor 145 and could be entered in the connected memory 150. Usage of the Hb parameter would allow the ESR processor 140 to calculate a standardized ESR value that is, for instance, normalized relative the Hb parameter for the same blood sample. Thus, the blood analyzing device 100 allows determination of normalized/standardized ESR values, which are not obtainable in a simple manner with the prior art techniques.

Figure 2A:
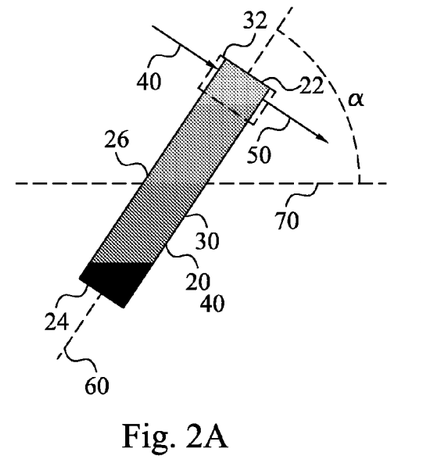
FIGS. 2A to 2D illustrate different photometry settings that can be used by the blood analyzing device according to the present invention.

FIGS. 2A to 2D illustrate in more detail the orientation of a cuvette 20 with a blood sample 30 during ESR measurements of the present invention. In FIG. 2A, the input light 40 incidences substantially perpendicular to the blood surface facing the light. The light passes through the blood sample 30 in a measuring volume 32 that is arranged in connection with a first end 22 of the cuvette 20. The output light 50 leaves the other side of the sample 30 and the detector will determine the absorbance and/or transmittance at one or more wavelengths.

It is evident from the figures, that the extension 26 in the first dimension is comparatively longer than the extension 22, 24 in the second dimension. The longitudinal axis 60 of the extension 26 in the first dimension is angled relative the horizontal axis with the non-zero angle α.

Compared to FIG. 2A, the input light 40 incidences in a measuring volume 34 positioned in connection with the opposite side 24 of the cuvette 20. Thus, whereas the blood volume in the measuring volume 32 of FIG. 2A will locally present a decreasing red blood cell concentration over time, the blood volume of the measuring volume 34 in FIG. 2B will see an increasing blood cell concentration due to the cell/stack sedimentation. Over time the absorbance will gradually reduce (transmittance gradually increase) in the measuring volume 32 of FIG. 2A, while gradually increase (transmittance gradually decrease) in the measuring volume 34 of FIG. 2B. Both of these positions of the measuring volume 32, 34 are excellent and well-adapted for ESR measurements, as the change in absorbance/transmittance is as largest in connection with the top end 22 and bottom end 24 portions of the measuring cuvette 20. Though might be far from ideal, the measuring volume 32, 34 could be placed anywhere along the cuvette length, with the disadvantage of requiring longer measurement times.

Figure 2B:
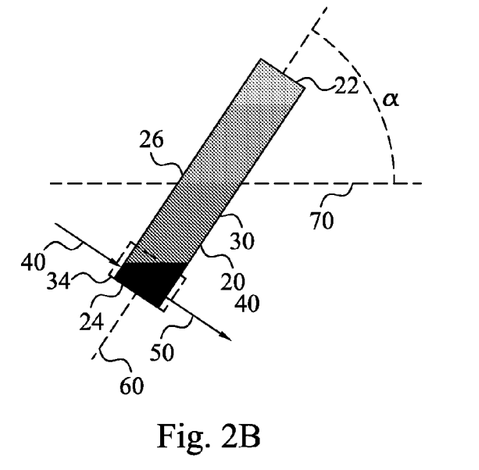

The measuring portion 32, 34 constitutes a sub-portion of the blood sample 30 in the cuvette 20. This sub-portion is typically no more than 75% of the total sample volume, preferably no more than 50%, such as no more than 40%, 30%, 25% or may be as small as 10% or even less of the total blood volume in cuvette portion 20 of the container 10.

Figure 2C:
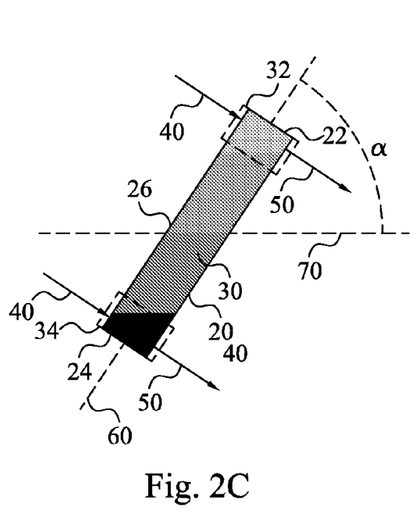

FIG. 2C combines the teachings of FIGS. 2A and 2B. Thus, the input light 40 is divided into two light beams, one entering the blood sample 30 in a first measuring volume 32 arranged in connection with the top end 22 of the cuvette 20, while the other enters the sample 30 in a second volume 34 in connection with the bottom end 24 of the cuvette 20. The detector could comprise one or more detector elements that are arranged for detecting output light 50 exiting the first measuring volume 32 and another/other detector elements detecting the output light 50 from the second measuring volume 34.

The Hb processor then uses the detector readings of the light originating from either volume 32, 34 in the determination of the kinetic information or preferably from both volumes 32, 34. The latter case could provide a more correct raw data basis as compared to only using light from one of the measuring volumes 32, 34 in the kinetics determination.

Figure 2D:
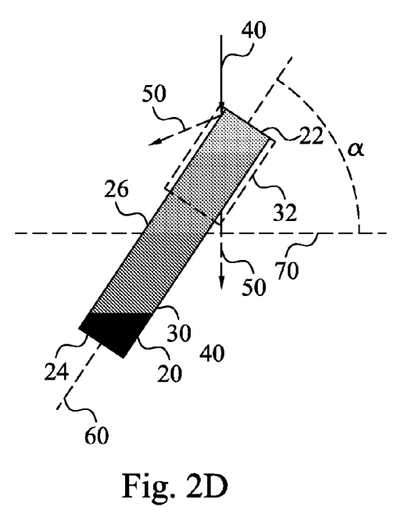

The input light 40 does not necessarily have to incident perpendicularly into the sample surface. FIG. 2D schematically illustrates that the light 40 could, for instance, be applied vertically down to the sample 30 in the measuring volume 32. As the cuvette 20 and the blood sample 30 are angled, the input light 40 will enter the light blood at an input angle different from 90°. Thus, the angle of incidence of the input light 40 can be in the range of from above 0° up to and including 90°.

The detector of the blood analyzing device of the present invention does not necessarily have to detect the light having passed through the blood sample 30 in the measuring volume 32 for the purpose of ESR determination. In clear contrast, the detector could be arranged for detecting output light reflected from the blood sample 30 in the measuring volume 32 as is schematically illustrated in FIG. 2D. In such a case, the processor performs the ESR determination based on the reflectance at one or more wavelengths of the output light 50.

Figure 3:
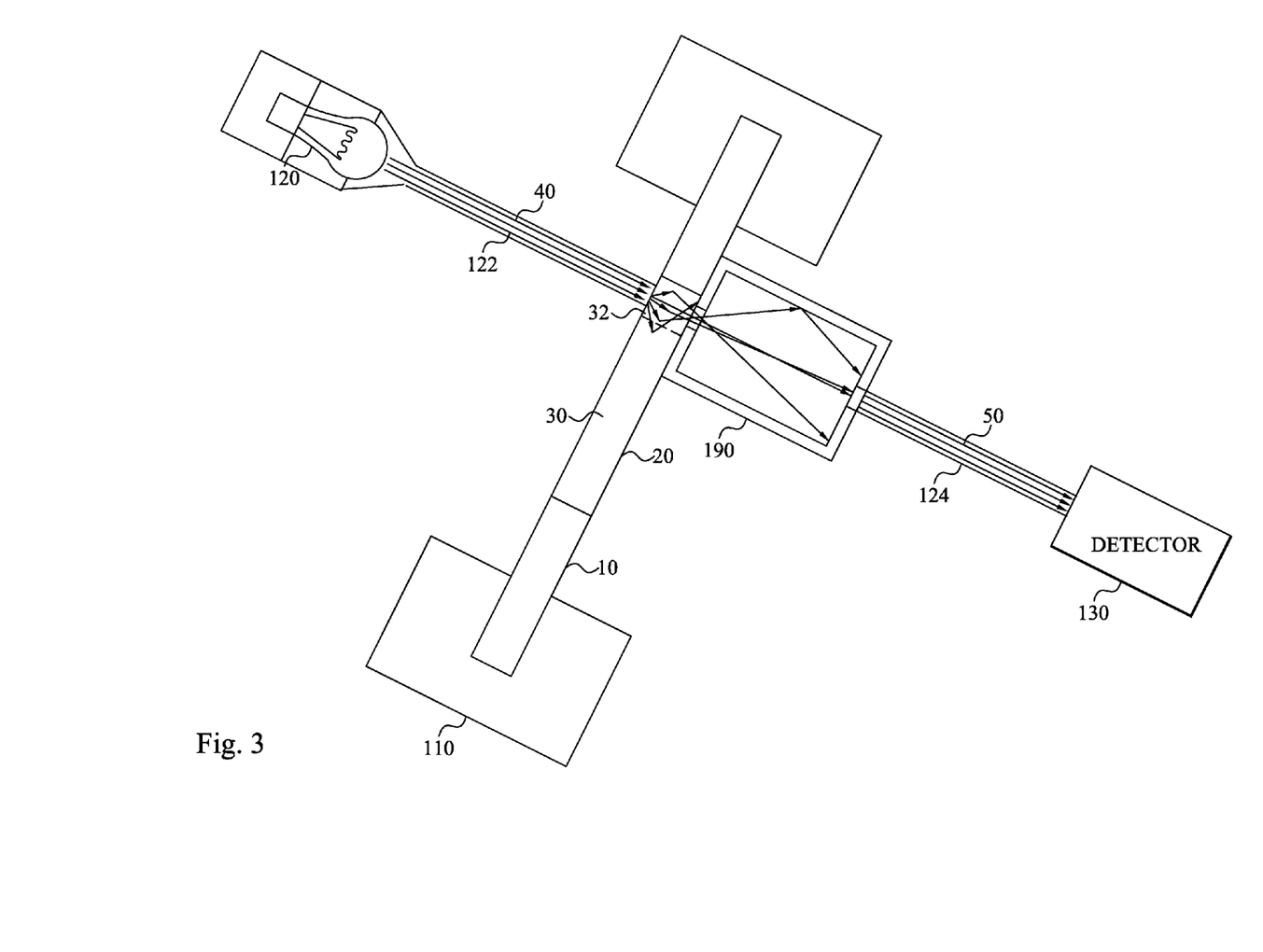
FIG. 3 schematically illustrates a portion of the light emitting, conducting and detecting path of the blood analyzing device according to an embodiment of the present invention.

FIG. 3 is a close-up view of a portion of the blood analyzing device of an embodiment of the present invention. The figure illustrates the light source 120 providing light to a measuring volume 32 of the blood sample 30 in the cuvette 20. In this embodiment, an input light guide 122 is arranged for directing the input light 40 from the source 120 into the measuring volume 32. The light guide 122 can be in the form of an optical fiber or cable that is able to provide a parallel bundle of light rays towards the sample 30. As the light passes through the blood sample 30 it will collide with particles, e.g. blood cells and stacks. Some light will be absorbed and some will scatter and continue in different direction.

A light trap 190 can be arranged in connection with the side of the cuvette 20 opposite to the side at which the light enters the sample 30 from the light guide. This light trap 190 will reduce the amount of scattered, i.e. non-parallel light from the output light. Such a light trap 190 can be designed in the form of cylinder having non-reflective or light-absorbing inner walls. The diameters of the entry opening and the exit opening of the light trap 190 are smaller than the inner diameter of the cylinder. Furthermore, the length of the trap 190 could be in the range of 5 to 30 times the diameter of the entry and exit openings. The substantially parallel (non-scattering) output light 50 exits the light trap 190 and may be guided up to the light detector 130 by an output light guide 124. This can also be in the form of an optical fiber or cable. For more information of the usage of a light trap 190 and a blood analyzing device equipped with such a light trap 190 reference is made to the International patent application number WO 2006/104451, the teaching of which is hereby incorporated by reference.

The usage of such a light trap 190 is in particular advantageous for the purpose of Hb measurements. However, it can also be used, without any negative impact, on the ESR measurements. As a consequence, a blood analyzing device of the invention adapted for performing both Hb and ESR measurements in a same blood sample loaded in a cuvette can advantageous be equipped with such a light trap 190.

Figure 4A:
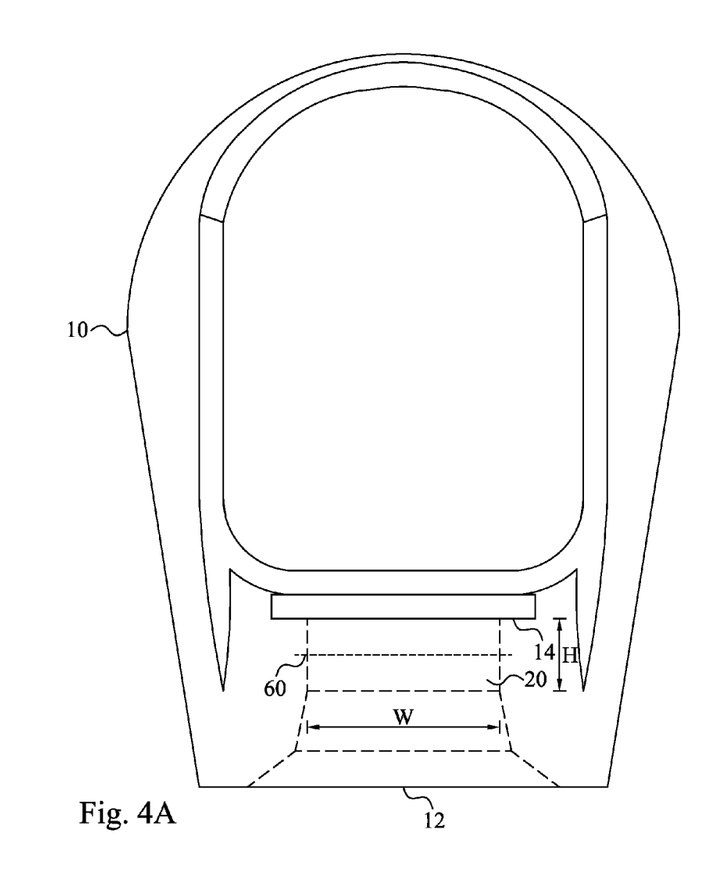
FIG. 4A is a schematic front view of a sample container that can be used in the blood analyzing device according to the present invention.
Figure 4B:
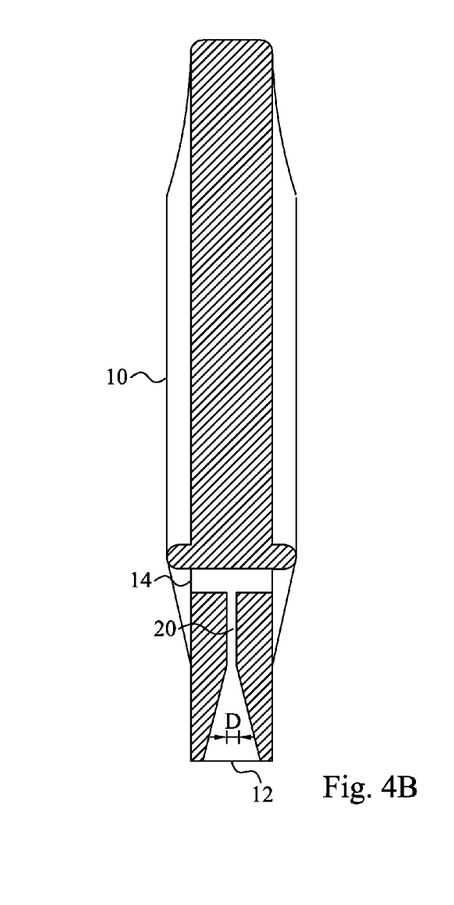
FIG. 4B is a cross-sectional view of the sample container of FIG. 4A.

FIG. 4A is schematic illustration of a sample container 10 that can be used in the blood analyzing device of the present invention. The container 10 comprises a cuvette 20 for containing the blood sample and into which the input light will be directed. An end side of the container 10 comprises an opening 12 that is contacted with blood causing the blood through the capillary effect to enter the container 10 and fill up the cuvette 20. The container 10 preferably also comprises an air outlet 14 allowing air present in the cuvette 20 to escape when blood is being drawn into the container 10. FIG. 4B is a cross-sectional view of the container 10, clearly illustrating the opening 12 and how it is in contact with the cuvette 20. In the figures, the dimensions of the cuvette 20 have been notified as height H, width W and depth D. The longitudinal axis 60 of the cuvette 20 here extends in the dimension of the width W of the cuvette 20. During operation, light will be incident on the surface defined by the height H and the width W and may then penetrate into the blood sample in the cuvette 20. In the case of absorbance/transmittance-based measurements, the light will pass through the depth D of the cuvette 20 and leave the opposite side of the height-width surface.

Figure 5:
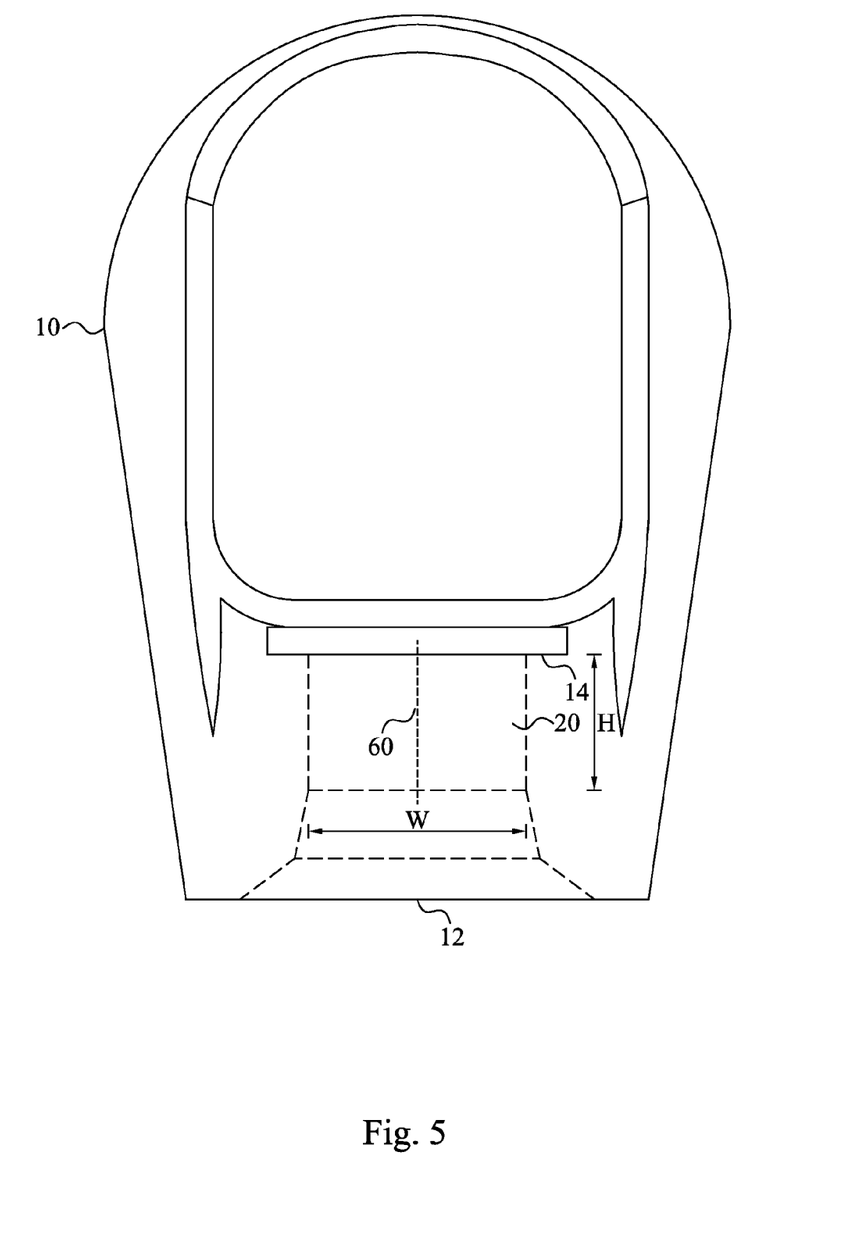
FIG. 5 schematically illustrates the movement of a sample container between a loading position and a measuring position.

FIG. 5 illustrates another sample container 10 that can be used according to the present invention. Compared to the container of FIGS. 4A and 4B, in this sample container 10 the longitudinal cuvette axis 60 extends in the same dimension as the cuvette height H.

Figure 6:
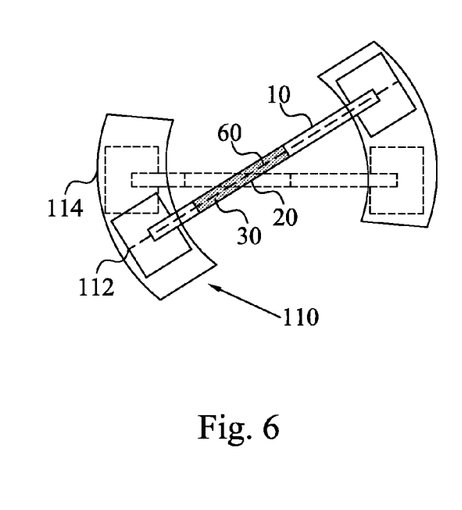
FIG. 6 is a schematic front view of another sample container that can be used in the blood analyzing device according to the present invention.

With a container 10 and cuvette 20 as illustrated in FIGS. 4A, 4B and 5, the container 10 can directly be inserted in the holder of the blood analyzing device in a position so that the longitudinal axis 60 of the cuvette 20 becomes angled relative a horizontal axis. Though, note that the container embodiment 10 of FIG. 5 has to be positioned differently in the device as compared to the container 10 of FIGS. 4A and 4B to get a non-zero angle between the longitudinal axis 60 and the horizontal axis. Alternatively, the container 10 could initially be placed in a loading position where the longitudinal axis 60, for instance, could be parallel with the horizontal axis as illustrated in the figure. Before performing the ESR measurements the container 10 is moved, typically rotated or turned (clockwise or counter-clockwise) as a key in a key hole, until the cuvette 20 comes in the measuring position. FIG. 6 schematically illustrates this procedure. The holder 110 here comprises a stationary holder portion 114 and a movable (rotatable) portion 112. The dashed lines illustrate the container 10 and the movable holder portion 112 in the loading position while the continuous lines depict the container 10 and movable portion 112 at the measuring position.

Figure 7:
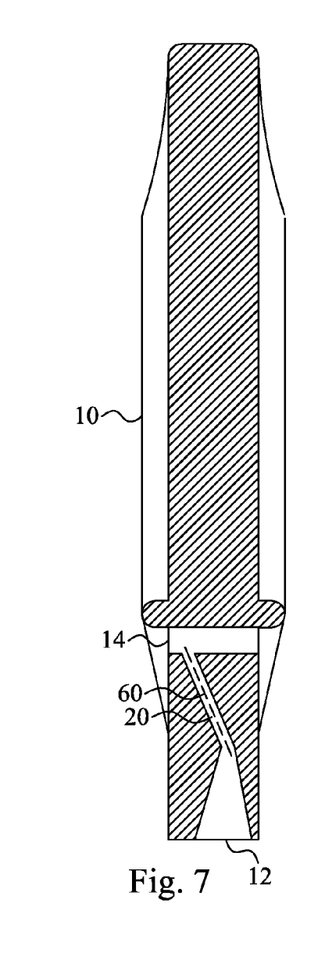
FIG. 7 is a cross-sectional view of a further sample container that can be used in the blood analyzing device according to the present invention.

FIG. 7 is a schematic illustration of another possible container embodiment 10 that can be used in the blood analyzing device of the present invention. In this embodiment, the cuvette 20 is manufactured to be angled relative the vertical axis of the container 10. The container 10 can then be placed in the blood analyzing device in a position as illustrated in FIG. 7 to provide the non-zero angle between the longitudinal axis 60 and the horizontal axis.

Figure 8:
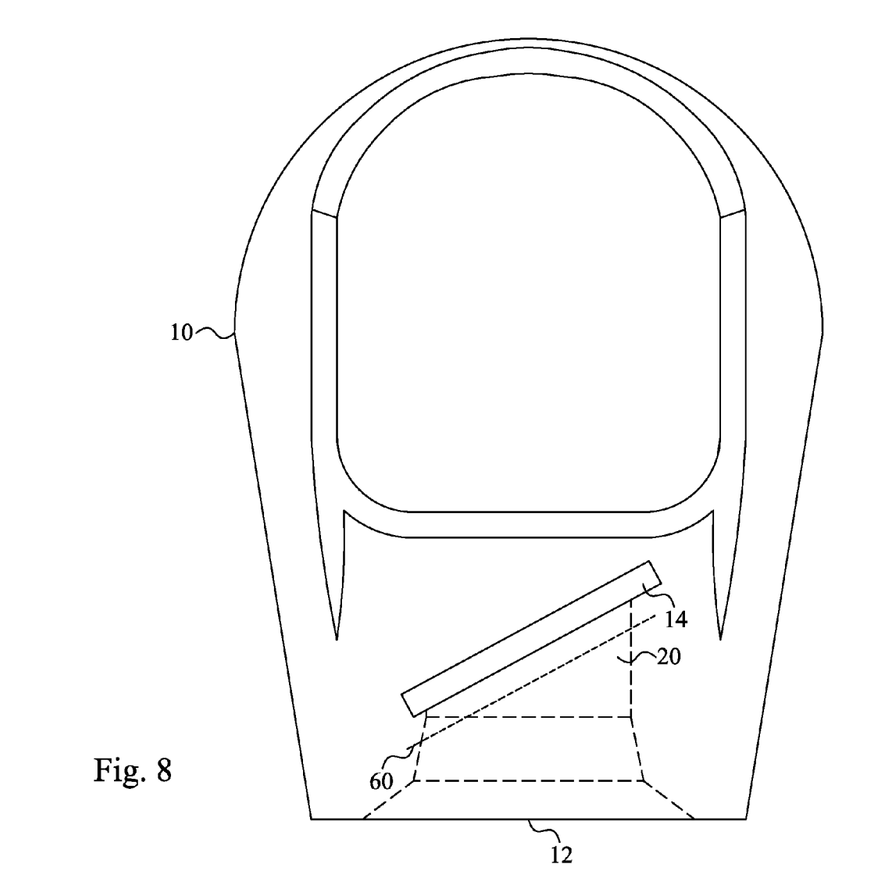
FIG. 8 is a schematic front view of yet another sample container that can be used in the blood analyzing device according to the present invention.

FIG. 8 is a further schematic illustration of a container 10 that can be used according to the present invention. Compared to FIGS. 4A and 5, the cuvette volume 20 is here reduced through the usage of an angled air outlet 14.

The container 10 of the present invention is made of materials traditional employed when manufacturing cuvettes, such as transparent or translucent plastics or glass material. The whole container 10 can made of the transparent material or only the portion of the container 10 through which light from a light source will pass into the cuvette 20 and the blood sample therein.

The blood analyzing device of the present invention is however not limited to usage with sample containers as illustrated in FIGS. 4A, 4B, 5, 7 and 8 but can be used in connection with other container and cuvette designs. Generally the container could have a size of one up to a few square centimeters. The cuvette is generally in the form of a rectangular parallelepided box (cuboid) or a cylinder, though other forms are still possible. The longitudinal extension could, for instance, be in the range of 1-10 mm, such as about 5 mm. The corresponding extension in the second extension could be about 0.01-1 mm, such as about 0.05-0.5 mm. The extension in the third dimension could be substantially the same as the longitudinal extension, i.e. for instance about 1-10 mm, such as about 5 mm. A total volume of the cuvette is typically in the range of 1-10 µl. When viewed in two dimensions the cuvette can be regarded as a slit having a first longitudinal extension in a first extension, a second comparatively shorter extension in a second dimension.

In some applications it can be preferred to actively prevent coagulation in the blood sample in the cuvette. In such a case, an anti-coagulant can be mixed with the blood prior being introduced in the cuvette. Alternatively, at least a portion of the inner surface of the container and/or cuvette being in contact the blood sample could be coated with an anti-coagulant. Any known such anti-coagulant could be used in connection with the present invention, such as citrate, EDTA, oxalate, heparin, direct thrombin inhibitors, such as argatroban, lepirudin, bivalirudin and ximelagatran, and vitamin K antagonists, such as warfarin, acenocoumarol and phenprocoumon, phenindione.

Figure 9:
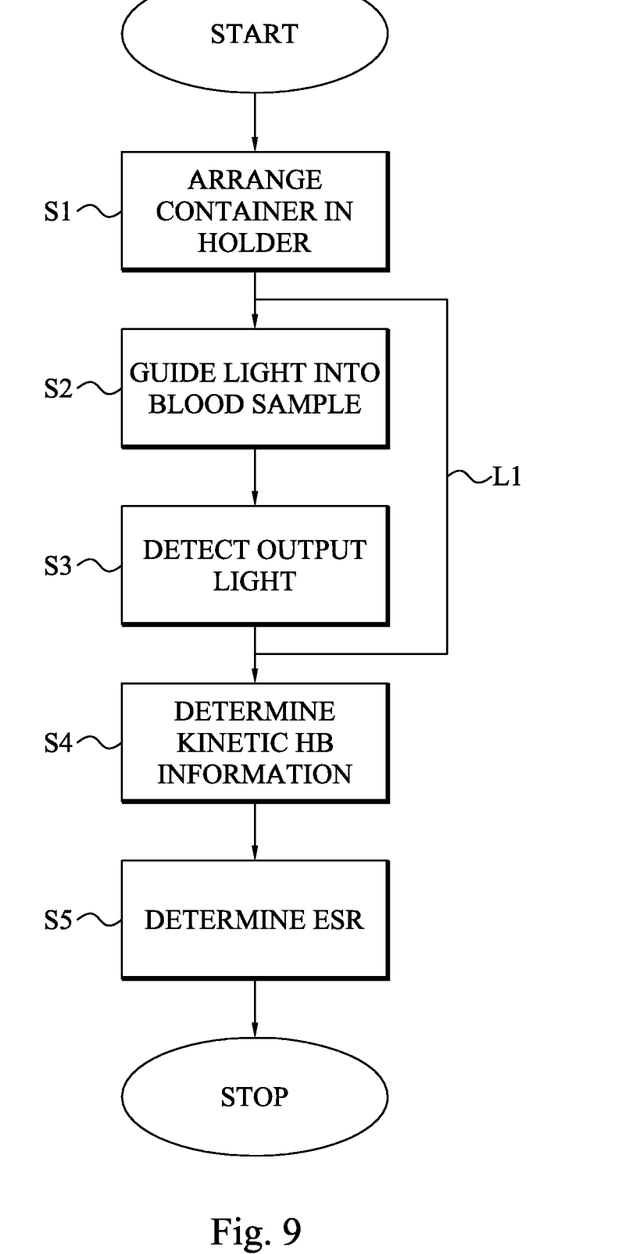
FIG. 9 is a flow diagram of a blood analyzing method according to an embodiment of the present invention.

FIG. 9 is a flow diagram illustrating a method of analyzing a blood sample contained in a cuvette of a sample container according to the present invention. The method starts in step S1, where the container is arranged in a holder in a measuring position in which a longitudinal axis of the cuvette is angled with a non-zero angle relative a horizontal axis. A next step S2 guides or directs light from a light source, possibly using a light guide or a system of light guides, into the blood sample in the cuvette. The light is selected to comprise at least one wavelengths for which at least one Hb species or fraction shows absorbance, preferably close to a maximum in absorbance (extinction coefficient). Output light originating from a measuring volume constituting a sub-portion of the blood sample is detected in step S3. The application of light and the corresponding detection of output light are conducted at multiple sample points, which is schematically illustrated by the line L1 in the figure. A next step S4 determines kinetic information reflective of the change in blood cell concentration (Hb value) over time in the measuring volume based on the detected output light. The determined kinetic information is then used in step S5, where the ESR in the blood sample is determined based on the kinetic information. The method then ends.

The detection of the output light may be performed continuously, periodically or intermittently within a measurement time period. The kinetic determination at step S4 could then use all or at least a portion of these multiple light detections in the calculation of the kinetic information.

Figure 10:
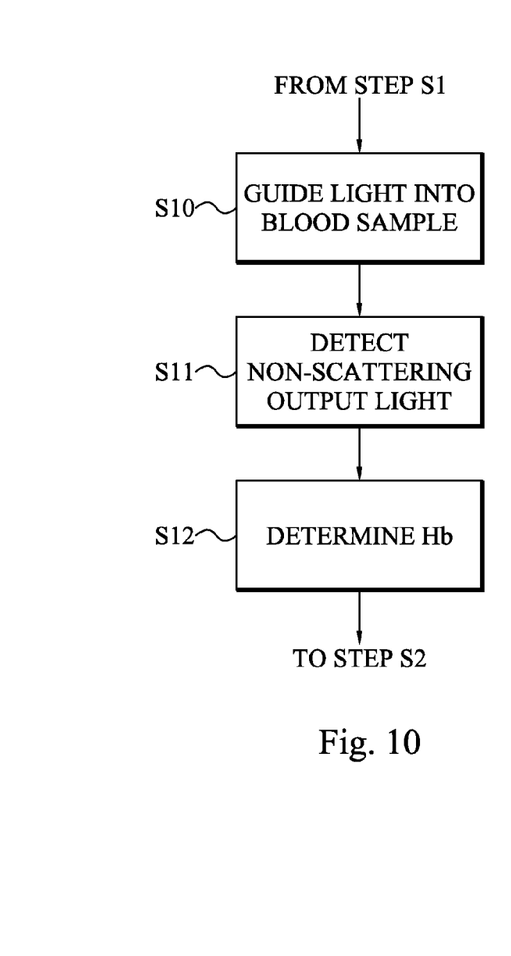
FIG. 10 is a flow diagram illustrating additional steps of the blood analyzing method of FIG. 9.

FIG. 10 is a flow diagram illustrating additional steps of the blood analyzing method of FIG. 9. The method continues from step S1 of FIG. 9. In a next step S10, light is guided from the light source into the blood sample. The light is allowed to pass through the blood sample in the cuvette and the resulting output light is detected in step S11. This light detection is preferably conducted based on non-scattering light by guiding the output light into a light trap before being detected by a light detector. A next step S12 determines at least one of total Hb concentration or the concentration of at least one Hb fraction in the blood sample based on the light detected in step S11. The method continues to step S2 of FIG. 9, where further spectroscopic measurements for determining the ESR in the blood sample is conducted. As has been previously discussed, this ESR determination can be performed at least partly based on the Hb value determined in step S12.

Figure 11:
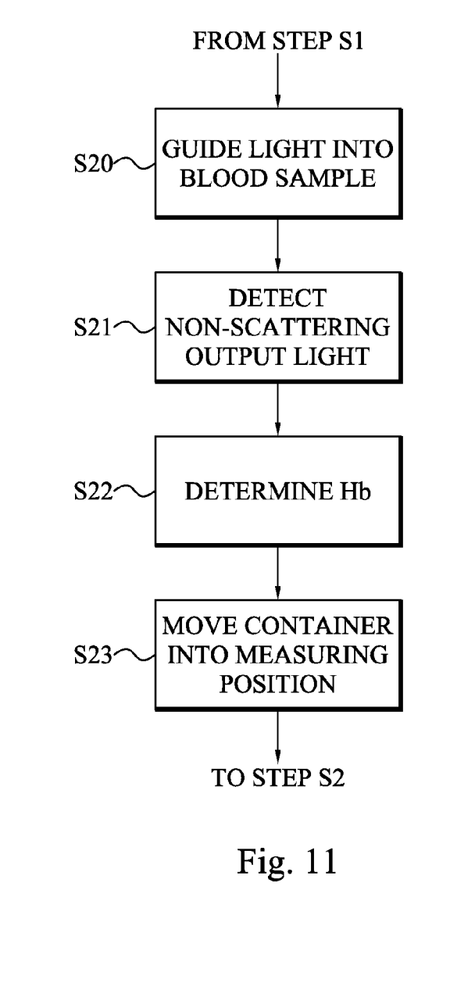
FIG. 11 is a flow diagram illustrating additional steps of the blood analyzing method of FIG. 9.

FIG. 11 is a flow diagram illustrating additional steps of the blood analyzing method of FIG. 9. The method continues from step S1 of FIG. 9, in which the container is initially placed in a loading position or Hb measuring position. At this position the longitudinal axis of the cuvette could be parallel with the horizontal axis. Light is then guided into the blood sample in step S20, the resulting output light is detected in step S1 and the total and/or fraction Hb is determined in step S22. These steps S20 to S22 are basically performed similar to the steps S10-S12 of FIG. 10. The container is then moved from this loading/Hb-measuring position into an ESR-measuring position, in which the angle between the longitudinal cuvette axis and the horizontal axis is adapted for ESR measurements, such as in the range of 45-60°. The method then continues to step S2 of FIG. 9.

The combined measurement of both Hb and ESR in a sample blood sample and using a same device is of great interest within the medical field as a general test for infections, a test for inflammatory processes or even a test for determining risk factor for a cardiovascular disease, such as heart attack.

Furthermore, today about 2 billion people in the developing countries suffer from anemia. Anemia is not a disease in itself but rather a symptom of several different conditions such as physical damage, malnutrition, and a variety of diseases. There is therefore a need for a simple and efficient way of discriminating between an anemia caused by malnutrition and an anemia caused by an infectious disease. The present invention is able to make this discrimination using a same device and same small blood sample.

The present invention can be used for determining ESR or ESR and Hb in a blood sample from an animal, preferably a vertebrate animal, more preferably a mammalian animal, such as a human being. The blood sample is preferably a whole blood sample.

It will be understood by a person skilled in the art that various modifications and changes may be made to the present invention without departure from the scope thereof, which is defined by the appended claims.

The invention claimed is:

1. A blood analyzing device comprising:
a holder including a stationary holder portion arranged for carrying a container having a cuvette comprising a blood sample, said cuvette having a longitudinal extension in a first dimension and a comparatively shorter extension in a second dimension, and a rotatable portion that rotates the stationary holder from a first position in which the stationary holder carries said container in a loading position such that the longitudinal axis of said cuvette is substantially parallel with a horizontal axis to a second position in which the stationary holder carries said container in a measuring position in which the longitudinal axis of said cuvette is angled with an angle larger than zero but smaller than ninety degrees relative to the horizontal axis;
a light source arranged for providing input light of a wavelength at which a hemoglobin, Hb, species has absorbance into said blood sample;
a light detector arranged for detecting output light from a measuring volume constituting a sub-portion of said blood sample at multiple time instances;
a Hb processor connected to said light detector and configured to determine kinetic information representative of a change in red blood cell concentration over time in said measuring volume based on output light detected by said light detector at said multiple time instances; and
an ESR processor connected to said Hb processor and configured to determine an erythrocyte sedimentation rate, ESR, in said blood sample based on said kinetic information received from said Hb processor, wherein,
said measuring volume is positioned in connection with a first end of said cuvette in said longitudinal extension, and
said measuring volume comprises a first measuring volume positioned in connection with said first end of said cuvette in said longitudinal extension and a second measuring volume positioned in connection with a second opposite end of said cuvette in said longitudinal extension.

2. The device according to claim 1, wherein said light source is arranged for providing input light of a wavelength at which a hemoglobin species has maximum absorbance into said blood sample.

3. The device according to claim 1, wherein said angle between said longitudinal axis of said holder and said horizontal axis is in an interval of from about 25° to about 80°.

4. The device according to claim 1, wherein said Hb processor is arranged for determining said Hb information based on said output light originating from said first measuring volume of said blood sample and said output light originating from said second measuring volume of said blood sample and being detected by said light detector.

5. The device according to claim 1, wherein said light detector is arranged for detecting, at least once within a measuring time interval following positioning of said container in said measuring position, light having passed through said blood sample over said comparatively shorter extension, and said Hb processor is arranged for determining at least one of total hemoglobin or at least one hemoglobin fraction in said blood sample based on said light having passed through said blood sample and being detected by said light detector.

6. The device according to claim 5, wherein said holder carries, when said light detector detects light having passed through said blood sample in said measuring time interval, said container in a loading position in which said longitudinal axis being substantially parallel with said horizontal axis.

7. The device according to claim 5, wherein said light detector is arranged for detecting said output light from said blood sample at said at multiple time instances occurring after the elapse of said measuring time.

8. The device according to claim 5, wherein said ESR processor is arranged for determining said erythrocyte sedimentation rate in said blood sample based on said kinetic information and said determined at least one of total hemoglobin or at least one hemoglobin fraction.

9. The device according to claim 1, wherein at least a portion of an inner container surface being in contact with said blood sample is coated with an anti-coagulant.

10. The device according to claim 1, wherein said holder carries said container in said measuring position in which said angle between said longitudinal axis of said holder and said horizontal axis is in an interval from about 45° to about 60°.

11. A blood analyzing device comprising:
a holder arranged for carrying a container having a cuvette comprising a blood sample, said cuvette having a longitudinal extension in a first dimension and a comparatively shorter extension in a second dimension, said holder carrying said container in a measuring position in which a longitudinal axis of said cuvette is angled with an angle larger than zero but smaller than ninety degrees relative to a horizontal axis such that a gradient in red blood cell sedimentation of the blood sample increases with respect to carrying said container in a position perpendicular to the horizontal axis;
a light source arranged for providing input light of a wavelength at which a hemoglobin, Hb, species has absorbance into said blood sample;
a light detector arranged for detecting output light from a measuring volume constituting a sub-portion of said blood sample at multiple time instances;
a Hb processor means for determining kinetic information representative of a change in red blood cell concentration over time in said measuring volume based on output light detected by said light detector at said multiple time instances; and
an ESR processor means for determining an erythrocyte sedimentation rate, ESR, in said blood sample based on said kinetic information received from said Hb processor, wherein
said measuring volume is positioned in connection with a first end of said cuvette in said longitudinal extension, and
said measuring volume comprises a first measuring volume positioned in connection with said first end of said cuvette in said longitudinal extension and a second measuring volume positioned in connection with a second opposite end of said cuvette in said longitudinal extension.

* * * * *